United States Patent [19]

Kuckertz

[11] 4,046,807
[45] Sept. 6, 1977

[54] PROCESS FOR PREPARING ACETIC ANHYDRIDE

[75] Inventor: Herbert Kuckertz, Bad Soden, Taunus, Germany

[73] Assignee: Hoechst Aktiengesellschaft, Frankfurt am Main, Germany

[21] Appl. No.: 625,692

[22] Filed: Oct. 24, 1975

[30] Foreign Application Priority Data

Oct. 26, 1974 Germany .............................. 2450965

[51] Int. Cl.² ....................... C07C 51/10; C07C 51/56
[52] U.S. Cl. ...................................... 260/549; 260/541
[58] Field of Search ................................ 260/549, 541

[56] References Cited

U.S. PATENT DOCUMENTS

| | | | |
|---|---|---|---|
| 2,593,440 | 4/1952 | Hagemeyer | 260/549 |
| 2,607,787 | 8/1952 | Mason | 260/549 |
| 2,730,546 | 1/1956 | Reppe et al. | 260/549 |
| 2,789,137 | 4/1957 | Reppe et al. | 260/549 |
| 3,927,078 | 12/1975 | Lapporte et al. | 260/549 |

*Primary Examiner*—Norman Morgenstern
*Attorney, Agent, or Firm*—Curtis, Morris & Safford

[57] ABSTRACT

Process for preparing acetic anhydride from acetic acid methyl ester and carbon monoxide in the presence of catalysts containing noble metals of the 8$^{th}$ sub-group of the periodic table or their compounds as well as iodine and/or iodine compounds.

11 Claims, No Drawings

PROCESS FOR PREPARING ACETIC ANHYDRIDE

The preparation of acetic anhydride on a technical scale is carried out by oxidation of acetaldehyde or by reaction of acetic acid with ketone.

It is also known to prepare acetic anhydride by the reaction of acetic acid methyl ester and carbon oxide while using nickel catalysts (German Pat. No. 921,987), but this possibility for producing acetic anhydride is plagued by fundamental disadvantages as compared to the above described technical methods of synthesis, so that the preparation by means of nickel catalyst never gained a wider significance. One of these disadvantages is, for example, that pressures of preferably above 300 bar, especially from 500 to 700 bar, are applied and that even under these pressures the reaction speed is slow; a further disadvantage is the fact that the operation is generally carried out in the presence of a solvent alien to the system, such as N-methylpyrrolidone and that, finally, larger quantities of catalyst and solvent have to be circulated.

Surprisingly, a process for preparing acetic anhydride from acetic acid methyl ester and carbon oxide has been found which comprises pressures of from 1 to 500 bar and at temperatures of from 50° to 250° C the reactants are conveyed over catalysts containing noble metals of the 8the subgroup of the periodic table or their compounds as well as iodine and/or iodine compounds.

Under the reaction conditions acetic acid methyl ester and carbon oxide react with each other in stoichiometric quantities. This does not mean, however, that strictly stoichiometric quantities have to be used for the reaction. Depending on the execution of the process there may be employed methyl acetate as well as carbon oxide at excess quantities.

As suitable starting materials may be considered, in addition to the commercially available methyl acetate, also mixtures of methyl acetate with other chemical compounds such as mixtures of methyl acetate with dimethyl ether. The latter is converted with carbonoxide under the reaction conditions, either partially or completely, to yield methyl acetate. In such a way it is possible, for example, to convert a mixture of this kind entirely to acetic anhydride.

However, the methyl acetate which is employed as starting product, may also contain methanol or minor quantities — e.g. from 1 to 5% — of water. In that case the result is not only acetic anhydride, but additionally a quantity of acetic acid being approximately equivalent to the quantity of methanol or water. This acetic acid is generally a desirable product, too, which can be separated easily — e.g. by distillation — from the main product acetic anhydride. The use of methylacetate-methanol-mixtures containing from 18 to 20% of methanol is very often particularly economical, since mixtures of this kind are obtained as azeotropics during other processes, e.g. upon esterification of acetic acid or transesterification of acetic acid esters with methanol.

The carbon oxide which is needed for the reaction must not be pure either, but may contain inert subcomponents such as nitrogen, carbon dioxide or methane.

The presence of large quantities, e.g. of from 5 to 50% by volume, of hydrogen in the reaction gas very often has a very favorable effect on the execution of the reaction. The slight formation of soot and carbon dioxide which can be observed ocasionally at reaction temperatures of above 150° C; is suppressed in the presence of hydrogen. From this fact results the advantage that in the presence of hydrogen the reaction can be carried out at high temperatures at high reaction speeds and prolonged life of the catalyst. On the other hand, when performing the reaction in the presence of hydrogen, an increased formation of acetic acid is generally noticed so that hydrogen is consumed.

The reaction is carried out at pressures of from 1 to 500 bar, preferably from 10 to 300 bar, particularly preferred are pressures comprised between 50 and 200 bar.

The reaction is performed at a temperature range from 50° to 250° C, preference is given to the operation at from 120° to 200° C, because this temperature range most often allows for an optimal relation of reaction speed to selectivity.

The reaction is executed in the presence of a catalyst which contains as essential components noble metals and/or noble metal compounds of the 8th subgroup of the periodic table, and of iodine or compounds thereof.

The noble metal component includes the following elements — either single or mixed—: ruthenium, rhodium, palladium, osmium, iridium and platinum. Especially efficient are catalysts containing rhodium or rhodium-compounds. Rhodium being a very expensive element, however, in many cases use of slightly less efficient elements might technically make sense, whereby especially palladium and platinum and their compounds may be considered. The initial form of the metal applied may vary widely.

The metals may be used, for example, as such. Preference is given to the use of finely distributed metals, such as they are formed e.g. by reducing salts, oxides or hydroxides in solution or on carrier catalysts. As examples for such metal catalysts may be cited raney-rhodium, raney-palladium, raney-platinum, rhodium on active coal. Alloys of the metals, besides the pure metals, e.g. the alloys with carbon and with the carbonyl-forming non-metals, prove to be well efficient, too. Alloys of metal with carbon are formed e.g. on those carrier catalysts which contain finely dispersed metals, by conveying carbon oxide over these catalysts at temperatures of above 100° C. Alloys of metals with carbonyl-forming non-noble metals may be prepared e.g. by reducing double salts such as cobalt-rhodium-III-chloride or nickel-rhodium-III-cyanides or of mixtures of the metal oxides, hydroxides or metal salts.

In many cases, however, the use of metal compounds instead of a metal or a metal alloy is preferred. Good catalytic properties are ascribed e.g. to metal halides such as $RuCl_3 . 3H_2O$, $RhCl_3 . 3H_2O$, $RhBr_3 . 2H_2O$, $RhJ_3$, $PdCl_2$, $IrCl_3$, $PtCl_2$ and $PtCl_4$, as well as oxides, hydroxides and metal salts of oxygen acids. As examples of groups of these substances may be cited $RuO_2$, $Rh_2O_3$, $Rh_2O_3 . H_2O$, $Rh(OH)_3$, sodium — rhodite, potassium platinite, PdO, $OsO_4$. Salts of inorganic acids, such as noble metal salts of nitric acid, phosphoric acid or sulfuric acid and their hydrates are efficient catalysts for the reaction, too, for example $RH(NO_3)_3 . 2H_2O$, $Rh_2(SO_4)_3$, platinum-IV-phosphate and palladium nitrate. Suitable catalysts are also the carboxylates of noble metals, such as the acetates, namely rhodium-III-acetate, palladium-III-acetate or platinum-IV-acetate. Very efficient catalysts are also complex compounds of noble metals, namely as well neutral complexes as also complex acids and complex salts, too. Ligands in such complexes are e.g. halogen, water, carbon oxide, phosphines or compounds of the trivalent nitrogen. As such compounds are to be considered e.g. $K_2RhBr_5$, $Rh[P(C_6H_5)_3]_2COCl$, $Rh(NH_3)_5Cl_3$, $H_2PtCl_6$, $Pt(CH_3)[P(CH_2H_5)_3]_2J_2$, $[(n-C_4H_9)_3P]_2PdJ_2$. Finally may be taken into consideration metal carbonyles, metal carbonyl halides or metal carbonyl halogen oxides as catalyst-components, e.g. $RH_2Cl_2O \cdot 3CO$, $Pt(CO)_n$, $PtCOJ_2$, $Pd(CO)_n$, $PdCOCl_2$.

The iodine-containing component of the catalyst may also vary widely, it may be added e.g. as elementary iodine or hydrogen iodide: Equally suitable starting compositions are inorganic salts such as sodium iodide, potassium iodide or cobalt iodide, as well as quaternary ammonium or phosphonium compounds such as tetramethyl ammonium iodide or tetraethyl phosphonium iodide which may be considered as catalyst components. In many cases, however, use will be made of organo-iodine-compositions as catalyst components, such as alkyl iodide, especially methyl iodide, or acyl iodides, especially acetyl iodide.

Other halogens, especially bromine or bromine compounds have a certain catalyzing effect, too.

It is recommendable to add to these essential catalyst components further promotors with e.g. the following assignments: to reduce the quantity needed of the aforementioned essential catalyst components, to improve the durability of the catalysts, to increase their selectivity, to improve the reaction speed. Such promotors are, for example complex-forming compounds such as alkyl phosphines or aryl phosphines or even organic nitrogen compounds such as pyridines, pyrrolidones, alkyl amines or N-alkyl-derivatives of aniline. Numerous metals or metal compounds, especially carbonyl-forming metals such as cobalt, nickel or iron show also a good effect as promotors.

The catalyst is used as a suspension, a solid or a solution. Preference is given to the use of catalyst solutions or catalyst suspensions. When using catalyst suspensions, the liquids consist essentially in the starting materials or the reaction products. Solid catalysts are preferably prepared as carrier catalysts while utilizing the usual carrier materials such as active coal, silica gel, silicates or aluminum oxides.

The concentration ratio of the aforementioned noble metals in the catalyst varies generally from 0.0001 to 10 weight %, preferably keeping within the range of from 0.001 to 1 weight %. As far as catalyst solutions and suspensions are concerned, good technical results will be obtained with low concentration rates, whilst carrier catalysts require higher concentration rates for an economically most interesting embodiment of the process. The concentration in iodine components of the catalyst varies widely, too. Very often the best suitable concentration ratio is not only determined by the noble metal components, but to a large extent also by the rest of the reactants involved in each case. The concentrations keep generally within from 0.01 to 20 weight %, but preferably from 0.1 to 10 weight %. Most often low reaction temperatures recommend high concentration rates, though at higher reaction temperatures the most economical embodiment of the process is brought about by lower concentration rates.

In relation to carbonylation reactions there have been described quite frequently in the past catalyst compositions being somewhat similar to those specified herein. However, no description has been given so far of an invention for the preparation of acetic anhydride under pressures below 500 bar from methyl acetate and carbon oxide at a high selectivity and with good conversion rates. It is known that by means of such catalysts carboxylic acids, especially acetic acid from methanol and carbon oxide, may be prepared from alcohols and carbon oxide. As far as the corresponding preparation of acetic acid from methanol and carbon oxide is concerned, it is a known fact that the reaction mixture include high concentrations in methyl acetate and that the reaction is leading to acetic acid at a high selectivity.

It is, therefore, a surprise that under the conditions of the present process acetic anhydride is obtained at a high selectivity.

It is further known that generally for carrying out the carbonylation reactions with catalysts which are similar to those according to the invention, the presence of large quantities of water are either required or at least very favorable.

Surprisingly, the reaction is running speedily under the reaction conditions as per the invention, i.e. also in absence of any noticeable quantities of water.

The process may be carried out either continuously or discontinuously. However, on an industrial scale preference is given to a continuous reaction.

When carrying out the reaction continuously by using catalyst liquids or suspensions, the reactor may consist, for example, of a tube mounted vertically which is operated either as a bubble reactor or as trickling-phase reactor. Carbon dioxide and methyl acetate are sent through this reactor. The reaction products are worked up e.g. by condensation and subsequent distillation. The non-reacted starting materials and the discharged catalyst, which is generally being formed during the work-up partially as column sump and partially as a low-boiling substance, are recycled into the reactor.

The acetic anhydride which is prepared according to the invention suits all known application fields, e.g. acetylation reactions or reacting with alcohols to yield acetic acid esters.

The process according to the invention may be applied also to the preparation of other anhydrides. As an example may be cited that the mixed anhydride of acetic acid and propionic acid may be prepared from ethylacetate and carbon oxide, or propionic anhydride may be obtained from propionic acid ethyl ester and carbon oxide.

The following Examples illustrate the process of the invention, especially concerning the preparation and efficiency of the catalysts.

EXAMPLE 1

The following substances are charged into a 200 ml agitator-autoclave:
50 g of methylacetate
5 g of methyl iodide
50 mg of $RhCl_3 \cdot 3H_2O$
200 mg of $P(C_6H_5)_3$ After having heated to 140° C, carbon oxide was introduced until the pressure of 80 bars was reached. The temperature was then gradually increased to 160° C and for three hours carbon oxide was metered in at such a rate that the pressure of 80 bar was maintained. The autoclave was then cooled and the pressure released. About 60 g of a liquid mixture containing about 27% of acetic anhydride were obtained. Further noticeable products were mainly 2% (approx.) of acetic acid. The mixture was submitted to a vacuum distillation at 20 mm Hg and at a heating temperature of 80° C so that a residue of about 7 g was obtained. This liquid residue contained about 70 weight % of acetic anhydride and was the catalyst of Example 2.

The vacuum distillation product was submitted to a fractional distillation under a normal pressure. About 3 g of methyl iodide (boiling point at 760 mm Hg: 42° C), about 35 g of methyl acetate (boiling point 57° C at 760 mm Hg), about 1 g of acetic acid (boiling point 118° C at 760 mm Hg) and about 11 g of acetic anhydride (boiling point from 139° to 140° C at 760 mm Hg) were obtained.

EXAMPLE 2

A 200 ml agitator-autoclave was charged with the following substances:
  50 g of methyl acetate
  3 g of methyl iodide
  7 g of the distillation residue of example 1

After having heated to 140° C carbon oxide was introduced until a pressure of 80 bar was reached. The temperature was then increased to 160° C and carbon oxide was metered in for three hours at such a quantity that the pressure of 80 bar was maintained. The autoclave was then cooled and the pressure released by a condensation trap maintained at −78° C. More than 99% by volume of the waste gas consists in carbon oxide.

About 64 g of a liquid mixture containing about 30% of acetic anhydride were obtained. While working-up by distillation under a normal pressure, about 2.5 g of methyl iodide and about 38 g of methyl acetate could be recovered. The following products were eliminated by distillation: about 1 g of acetic acid and about 12 g of acetic anhydride leaving behind about 7.5 g of sump which consisted in about 70 weight % of acetic anhydride. This sump product may be re-used as catalyst component.

EXAMPLES 3 – 12

Further Examples were carried out in analogy to Example 1, while varying some catalyst components. The following details of Example 1 were retained: the quantity of methyl acetate employed (50 g), the quantity of methyl iodide used (5 g), the reaction temperature (160° C), the reaction pressure (80 bar) and the reaction time (3 hours).

The variations of the catalyst and the quantities of acetic anhydride obtained are stated in the following table.

TABLE

| Example | Catalyst Noble metal | Promoter | Acetic anhydride (g) |
|---|---|---|---|
| 3 | 80 mg RhCl$_3$ . 3H$_2$O | — | 10 |
| 4 | 25 mg RhCl$_3$ . 3H$_2$O | 200 mg CO(OAc)$_2$ 200 mg P (C$_3$H$_6$)$_2$ | 15 |
| 5 | 200 mg Rh(NH$_3$)$_5$Cl$_3$ | — | 11 |
| 6 | 200 mg Rh[P(C$_6$H$_5$)$_3$]$_2$COCl | — | 14 |
| 7 | 200 mg Pd(OAc)$_2$ | 200 mg P (C$_6$H$_5$)$_3$ | 6 |
| 8 | 200 mg raney-Pd | " | 5 |
| 9 | 200 mg PtCl$_4$ | " | 7 |
| 10 | 200 mg IrCl$_3$ | " | 4 |
| 11 | 200 mg RuCl$_3$ . 3H$_2$O | " | 4 |
| 12 | 200 mg OsO$_4$ | " | 3 |

The quantity of acetic anhydride as stated in the table refers to the quantity which was obtained by complete work-up of the reaction products, i.e. no catalyst components were recycled to acetic anhydride solution according to examples 1 and 2. All tests showed a selectivity of the reaction of more than 90%.

The most important by-product was acetic acid.

EXAMPLE 13

This Example illustrates the effect of the presence of hydrogen.

The following substances were charged into a 200 ml agitator-autoclave:
  50 g of methyl acetate
  5 g of methyl iodide
  80 mg of RhCl$_3$ . 3H$_2$O
  80 mg of P(C$_6$H$_5$)$_3$ The test was then continued as follows:

a. After heating to 180° C, carbon dioxide was added until the pressure reached 80 bar. This pressure of 80 bar was maintained by constantly metering in further carbon dioxide. The autoclave was cooled after 3 hours and the pressure released. The release gas contained about 1% of carbon dioxide. 60 g of a dark liquid containing fine particles of carbon black remained in the autoclave. About 25% of acetic anhydride and about 1% of acetic acid were also contained in this liquid.

b. Prior to heating to 180° C hydrogen was introduced at such a rate that the pressure was adjusted to 10 bar. After having completed the heating process to 180° C, the pressure was increased to 80 bar by means of carbon oxide and was maintained at this value by constantly metering in further carbon oxide. The autoclave was cooled after three hours and the pressure released. The release gas contained less than 0.1% of carbon dioxide. About 61 g of liquid remained in the autoclave which had a dark colour shade, but did not contain any particles of carbon black. This liquid contained about 19% of acetic anhydride and about 12% of acetic acid.

EXAMPLE 14

The following substances were charged into a 200 ml agitator-autoclave:
  30 g of methyl acetate
  20 g of methyl iodide/methanol at the weight ratio of 82:18 (azeotropic)
  1 g of iodine
  200 mg of RhCl$_3$ . 3H$_2$O
  200 mg of P(C$_6$H$_5$)$_3$ After heating to 160° C, the pressure was increased to 150 bar by means of carbon oxide. This pressure of 150 bar was maintained for 5 hours by constantly metering in further carbon oxide. The autoclave was then cooled and the pressure released. We obtained about 60 g of a liquid reaction mixture containing 12% of acetic acid and about 35% of acetic anhydride. 30 g of methyl acetate were recovered by means of fractional distillation. The products, namely 6.5 g of acetic acid (boiling point 118° C under a pressure of 760 mm Hg) and 15 g of acetic anhydride (boiling point 139° – 140° C under a pressure of 760 mm Hg), were obtained by distillation. After 8 g of a liquid distillatin residue remained, consisting of about 60 weight % of acetic anhydride. This distillation residue was used as catalyst for carrying out the reaction of Example 15.

EXAMPLE 15

The following substances were charged into a 200 ml agitator-autoclave:
- 30 g of methyl acetate
- 20 g of methyl acetate/methanol at the weight ratio of 82:18 (azeotropic)
- 8 g of the distillation residue of example 14

After heating to 160° C, the pressure was increased to 150 bar by means of carbon oxide and maintained at this level for 5 hours. The autoclave was then cooled and the pressure released. We obtained about 67 g of a liquid reaction mixture. About 30 g of methyl acetate were recovered by distillation, subsequently 7 g of acetic acid (boiling point 118° C under a pressure of 760 mm Hg) and 20 g of acetic anhydride (boiling point 139° – 140° C under a pressure of 760 mm Hg) were distilled off the reaction mixture. The remaining distillation residue of from 9 to 10 g was still containing about 60% of acetic anhydride. It may be used as catalyst for another preparation of acetic anhydride and acetic acid.

EXAMPLE 16

250 ml of active coal having a grain size of from 6 to 8 mm were soaked with an aqueous solution containing 0.5 g of $RhCl_3 . 3H_2O$ and 1 g of KJ. The impregnated coal was then dried in a nitrogen current at 60° C up to the constant weight.

The carrier catalyst being prepared in such a way was charged into a reactor consisting in a steel tube of a 25 mm diameter and a 750 mm length. A gas mixture of per hour 100 Nl (= Normal liter at 0° C and 760 mm Hg) of CO, 20 Nl of methyl acetate and 1 Nl of methyl iodide, at a temperature of about 160° C and under a pressure of 10 bar, was conveyed over the catalyst. An exothermic reaction took place. The reactor was therefore cooled, in order to maintain a reaction temperature of 160° C.

The gas mixture was cooled to about 25° C under a pressure of about 10 bar while leaving the reactor. About 70 g per hour of a liquid were produced, which contained — besides about 3 g of methyl iodide and about 60 g of methyl acetate — about 6 g of acetic anhydride.

More than 90% by volume of the gaseous phase, which could not be condensed at 25° C, consisted in carbon oxide. The only further substantial components were methyl iodide and methyl acetate. The liquid was worked-up by distillation under normal pressure.

The gaseous phase which could not be condensed and the recovered quantities of methyl acetate and methyl iodide were fed back into the reactor.

The consumed quantity of methyl acetate and carbon oxide were replenished by fresh substances, so that the aforementioned quantities of the starting materials were maintained. As far as methyl iodide was concerned, there were only very small quantities to be replaced, i.e. quantities inferior to 0.1 Nl p/h.

The selectivity of the formation of acetic anhydride was 90% calculated on methyl acetate and carbon oxide. The most important by-product was acetic acid.

What is claimed is:

1. A process for the preparation of acetic anhydride which comprises reacting a mixture consisting essentially of acetic acid methyl ester and carbon monoxide at a pressure of 1 to 500 bar and at temperature of from 50 to 250° C and carrying out said reaction in the presence of a catalyst containing a noble metal of the 8th subgroup of the Periodic Table.

2. The process of claim 1, which comprises carrying out the reaction at a pressure of 10 to 300 bar.

3. The process of claim 1 which comprises carrying out the reaction at a temperature of 120° to 200° C.

4. The process of claim 1, which comprises carrying out the reaction in the presence of hydrogen.

5. The process of claim 1, wherein the noble metal catalyst contains rhodium.

6. The process of claim 1, wherein the catalyst contains a member selected from the group consisting of iodine and iodine compounds.

7. The process of claim 1, wherein the catalyst contains a member selected from the group consisting of alkyl iodide and acyl iodide compounds.

8. A process for the preparation of acetic anhydride which comprises reacting a mixture consisting essentially of acetic acid methyl ester and carbon monoxide at a temperature of about 120° to 200° C and a pressure of up to 200 bar and carrying out said reaction in the presence of a catalyst which contains a noble metal of the eighth subgroup of the Periodic Table.

9. The process of claim 8 wherein the selectivity of the reaction to the production of acetic anhydride is more than 90%.

10. The process of claim 8 wherein the reaction is carried out in about 3 hours.

11. The process of claim 8 wherein the reaction is carried out in about 5 hours.

* * * * *